United States Patent
Sowards et al.

(10) Patent No.: US 12,354,738 B2
(45) Date of Patent: Jul. 8, 2025

(54) RFID ENABLED MEDICAL DEVICES AND ASSOCIATED SYSTEMS

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US); Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 329 days.

(21) Appl. No.: 17/489,411

(22) Filed: Sep. 29, 2021

(65) Prior Publication Data

US 2022/0101991 A1     Mar. 31, 2022

Related U.S. Application Data

(60) Provisional application No. 63/085,870, filed on Sep. 30, 2020.

(51) Int. Cl.
*G16H 40/63* (2018.01)
*A61B 90/98* (2016.01)
*G06K 7/10* (2006.01)

(52) U.S. Cl.
CPC .............. *G16H 40/63* (2018.01); *A61B 90/98* (2016.02); *G06K 7/10366* (2013.01)

(58) Field of Classification Search
CPC ............ A61B 1/00059; A61B 1/00165; A61B 1/3137; A61B 2090/0804;
(Continued)

(56) References Cited

U.S. PATENT DOCUMENTS

| | | |
|---|---|---|
| 7,545,272 B2 | 6/2009 | Goodnow et al. |
| 8,388,541 B2 | 3/2013 | Messerly et al. |
| (Continued) | | |

FOREIGN PATENT DOCUMENTS

| | | |
|---|---|---|
| WO | 2019/147857 A1 | 8/2019 |
| WO | 2020/041717 A1 | 2/2020 |
| WO | 2021/045995 A1 | 3/2021 |

OTHER PUBLICATIONS

PCT/US2021/052695 filed Sep. 29, 2021 International Search Report and Written Opinion dated Mar. 21, 2022.

*Primary Examiner* — Omer S Khan
(74) *Attorney, Agent, or Firm* — Rutan & Tucker LLP

(57) ABSTRACT

Disclosed herein are RFID enabled medical device systems including an RFID emitter configured to provide an interrogation signal that impinges on an RFID tag associated with a medical device to trigger a response signal. The response signal can indicate and presence or absence of the medical device proximate to the RFID emitter. A console communicatively coupled to the RFID emitter can determine, record, and analyze procedural or usage information about the medical device. Further information about the medical device can be encoded within the response signal and provided to the console. Console settings can be automatically updated based on the information within the response signal. Additional modalities are also contemplated including optical image recognition of medical device kits. Further AR viewers can provide image overlays to guide a user in correct procedure. Procedural compliance can be automatically recorded and monitored.

15 Claims, 5 Drawing Sheets

(58) Field of Classification Search
CPC .... A61B 2090/0805; A61B 2560/0223; A61B 2562/085; A61B 5/6852; A61B 90/98; G06K 7/10366; G16H 40/63
See application file for complete search history.

(56) References Cited

U.S. PATENT DOCUMENTS

| | | |
|---|---|---|
| 8,781,555 B2 | 7/2014 | Burnside et al. |
| 8,849,382 B2 | 9/2014 | Cox et al. |
| 9,445,743 B2 | 9/2016 | Kassab |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,636,031 B2 | 5/2017 | Cox |
| 9,649,048 B2 | 5/2017 | Cox et al. |
| 9,757,200 B2 | 9/2017 | Magee et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| 10,524,691 B2 | 1/2020 | Newman et al. |
| 10,751,509 B2 | 8/2020 | Misener |
| 11,000,205 B2 | 5/2021 | Kassab et al. |
| 2002/0027507 A1* | 3/2002 | Yarin ............ G16H 20/13 705/2 |
| 2006/0142739 A1* | 6/2006 | DiSilestro ........ A61B 90/90 606/1 |
| 2014/0197954 A1* | 7/2014 | Caputo ............ G16B 50/00 340/572.1 |
| 2015/0080716 A1 | 3/2015 | Powers et al. |
| 2016/0089530 A1* | 3/2016 | Sathe .............. A61M 39/20 604/533 |
| 2017/0251922 A1 | 9/2017 | Roesicke et al. |
| 2018/0082480 A1* | 3/2018 | White ............. A61B 90/94 |
| 2018/0116551 A1 | 5/2018 | Newman et al. |
| 2018/0310955 A1* | 11/2018 | Lindekugel ...... A61B 90/98 |
| 2020/0197681 A1 | 6/2020 | Bodnicki et al. |

* cited by examiner

RFID ENABLED MEDICAL DEVICES AND ASSOCIATED SYSTEMS

PRIORITY

This application claims the benefit of priority to U.S. Patent Application No. 63/085,870, filed Sep. 30, 2020, which is incorporated by reference into this application.

SUMMARY

Embodiments disclosed herein are directed to radio frequency identification ("RFID") enabled medical devices, systems and associated methods thereof. An RFID tag can be coupled with a medical device and can be interrogated by an RFID emitter to determine information about the medical device. This information can be used to automatically update an external computing system, console, or the like, can track a location of the medical device, or monitor correct usage of the medical device. Information about the usage of one or more medical devices can be used to monitor compliance or improve future systems.

Disclosed herein is an RFID enabled medical device system including, an RFID tag associated with a medical device, and an RFID emitter communicatively coupled with a console configured to provide an interrogation signal that can impinge on the RFID tag to induce a response signal, the response signal configured to provide information to the console about the medical device.

In some embodiments, the medical device is a fiber optic stylet configured to map a vascular pathway and the RFID tag is disposed within a hub disposed at a proximal end of the stylet, the information provided to the console includes calibration information. The RFID emitter is configured to trigger the response signal when the RFID tag is within a range of between 1 cm and 50 m. The RFID emitter is configured to trigger the response signal when the RFID tag is within a range of less than 1 cm. The RFID emitter is configured to induce the response signal when the hub of the stylet is coupled to a connector that is communicatively coupled with the console.

In some embodiments, the medical device is disposed within a packaging and the RFID tag is disposed on the packaging. The RFID tag provides calibration information for the medical device to the console. The medical device can include one of an indwelling device, a procedural device, a packaging of the medical device, a maintenance device, or a personnel identification equipment. The information provided to the console includes one of medical device identification, medical device specification information, personnel information, analytics information, compliance information, post-procedure and identification information, or automatic device update information. The RFID emitter is configured to write information to the RFID tag. In some embodiments, information written to the RFID tag includes one of medical device identification, medical device specification information, personnel information, analytics information, compliance information, post-procedure and identification information, or automatic device update information.

Also disclosed herein is an RFID enabled medical device kit including, a tray including a compartment configured to contain a medical device, a RFID tag associated with one of the tray or the medical device, and an RFID emitter communicatively coupled to a console and configured to provide an interrogation signal that can impinge on the RFID tag to trigger a response signal, the response signal configured to provide information to the console about the tray or the medical device.

In some embodiments, the RFID emitter is disposed within a support surface configured to support the tray. The support surface includes a table, a cart, a rolling stand, or a flexible membrane. The RFID emitter is disposed within the tray. The RFID emitter is configured to provide a first interrogation signal which can induce a first response signal from a first medical device and a second response signal from a second medical device. A first RFID emitter is configured to provide a first interrogation signal which can induce a first response signal from a first medical device and a second RFID emitter is configured to provide a second interrogation signal which can induce a second response signal from a second medical device.

In some embodiments, the RFID emitter is configured to trigger the response signal when the RFID tag is within a range of less than 1 cm. The medical device can include one of an indwelling device, a procedural device, a packaging of the medical device, a maintenance device, or a personnel identification equipment. The information provided to the console includes one of medical device identification, medical device specification information, personnel information, analytics information, compliance information, post-procedure and identification information, or automatic device update information. The RFID emitter is configured to write information to the RFID tag. In some embodiments, information written to the RFID tag includes one of medical device identification, medical device specification information, personnel information, analytics information, compliance information, post-procedure and identification information, or automatic device update information. In some embodiments, the RFID enabled medical device kit further includes an AR viewer communicatively coupled to the console and configured to provide an image overlay of the medical device kit to indicate an order in which a first medical device and a second medical device is used.

Also disclosed is an optically enabled medical device system including, a tray including a compartment configured to contain a medical device, a camera configured to image an upper surface of one of the tray or the medical device, and a console communicatively coupled to the camera and configured to receive the image from the camera and determine a presence or an absence of a medical device from the kit.

In some embodiments the compartment includes a symbol, barcode, or QR code that is detectable by the camera when the medical device is absent from the compartment, the console configured to interpret information about the medical device from the symbol, barcode, or QR code. In some embodiments, the optically enabled medical device system further includes an AR viewer communicatively coupled to the console and configured to provide an image overlay of the medical device kit to indicate an order in which a first medical device and a second medical device is used.

Also disclosed is a method of calibrating a medical device system including, providing an interrogation signal by an RFID emitter communicatively coupled to a console, impinging the interrogation signal on an RFID tag coupled to a medical device, providing information about the medical device, encoded within a response signal, to the console, and calibrating the console to the medical device using the information encoded within the response signal.

In some embodiments, the medical device is a fiber optic stylet configured to map a vascular pathway and the RFID tag is disposed within a hub disposed at a proximal end of the stylet. The RFID emitter is configured to induce the response signal when the RFID tag is within a range of less than 1 cm.

Also disclosed is a method of using a medical device kit including, providing a first interrogation signal from an RFID emitter that is communicatively coupled with a console, triggering a first response signal from an RFID tag by the interrogation signal impinging on the RFID tag, the RFID tag coupled to a medical device, determining a start time when the interrogation signal fails to trigger a response signal, and determining a finish time when the interrogation signal triggers a response signal.

In some embodiments, the first interrogation signal triggers a second response signal from a second RFID tag coupled to a second medical device. A second interrogation signal triggers a second response signal from a second RFID tag coupled to a second medical device. The medical device includes one of an indwelling device, a procedural device, a packaging of the medical device, a maintenance device, or a personnel identification equipment. The console receives and determines information about the kit including one of medical device identification, medical device specification information, personnel information, analytics information, compliance information, post-procedure and identification information, or automatic device update information.

Also disclosed is an RFID enable ultrasound system including, an ultrasound console having an ultrasound probe communicatively coupled thereto, and an RFID emitter communicatively coupled with the ultrasound console and configured to provide an interrogation signal that can impinge on a RFID tag disposed on a medical device to induce a response signal, the response signal configured to provide information to the ultrasound console about the medical device.

In some embodiments, the medical device is part of a medical device kit, the medical device kit includes a second RFID tag configured to provide a second response signal in response to the interrogation signal. The RFID emitter is disposed on the ultrasound probe. The ultrasound console includes an image recognition logic communicatively coupled to one of an optical camera, an ultrasound logic, or a user interface display logic to determine information about one of the medical device, a medical device kit, a clinician or a patient.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
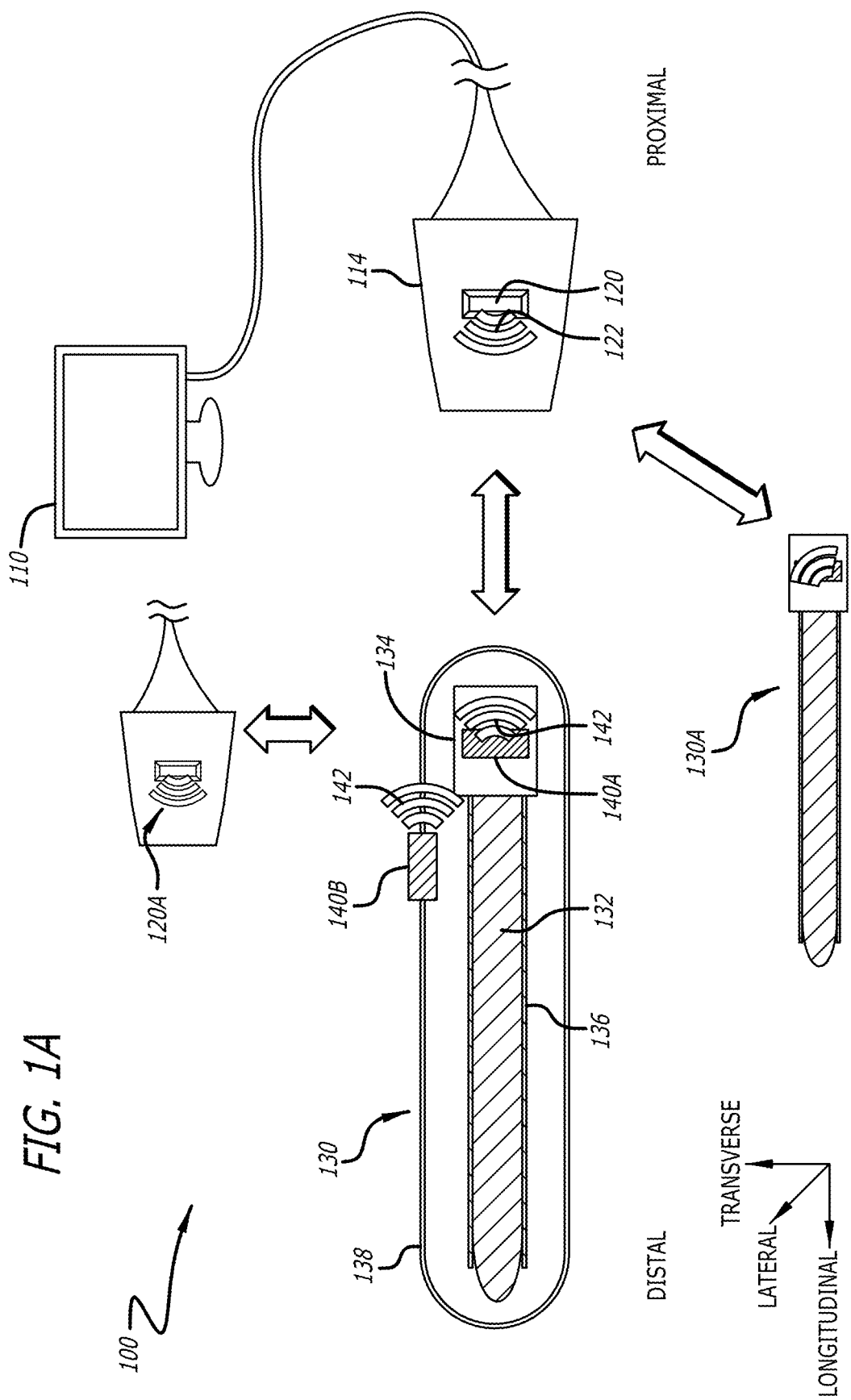
FIG. 1A illustrates an exemplary medical system including an RFID tag coupled to a medical device and an RFID emitter coupled to a console, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a stylet disclosed herein includes a portion of the stylet intended to be near a clinician when the stylet is used on a patient. Likewise, a "proximal length" of, for example, the stylet includes a length of the stylet intended to be near the clinician when the stylet is used on the patient. A "proximal end" of, for example, the stylet includes an end of the stylet intended to be near the clinician when the stylet is used on the patient. The proximal portion, the proximal end portion, or the proximal length of the stylet can include the proximal end of the stylet; however, the proximal portion, the proximal end portion, or the proximal length of the stylet need not include the proximal end of the stylet. That is, unless context suggests otherwise, the proximal portion, the proximal end portion, or the proximal length of the stylet is not a terminal portion or terminal length of the stylet.

With respect to "distal," a "distal portion" or a "distal end portion" of, for example, a stylet disclosed herein includes a portion of the stylet intended to be near or in a patient when the stylet is used on the patient. Likewise, a "distal length" of, for example, the stylet includes a length of the stylet intended to be near or in the patient when the stylet is used on the patient. A "distal end" of, for example, the stylet includes an end of the stylet intended to be near or in the patient when the stylet is used on the patient. The distal portion, the distal end portion, or the distal length of the stylet can include the distal end of the stylet; however, the distal portion, the distal end portion, or the distal length of the stylet need not include the distal end of the stylet. That is, unless context suggests otherwise, the distal portion, the distal end portion, or the distal length of the stylet is not a terminal portion or terminal length of the stylet.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

As shown in FIG. 1, and to assist in the description of embodiments described herein, a longitudinal axis extends substantially parallel to an axial length of a fiber optic stylet 132. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

The present disclosure relates generally to RFID or optically enabled medical devices, systems and associated methods. FIG. 1A shows an exemplary RFID enabled medical device system ("system") 100. The system 100 generally includes an external computing device ("console") 110 including an RFID emitter 120 and a medical device 130 that includes an RFID tag 140. As used herein the external computing device 110 can include a console, workstation, computer, laptop, handheld device, mobile device, or the like configured to receive, analyze, or display information received from one or more of the medical device(s) 130 or from additional networked computing devices communicatively coupled thereto, as described in more detail herein. In an embodiment, the medical device 130 can be a fiber optic stylet ("stylet") 132. In an embodiment, the medical device 130 can be a disposable, single use medical device. However, it will be appreciated that this is not intended to be limiting and the medical device 130 can include various other medical devices, as described in more detail herein.

In an embodiment, the fiber optic stylet 132 can be supported by a stylet hub 134 and include the RFID tag 140 disposed therein. In an embodiment, the RFID tag 140 can be disposed on a packaging 138 that contains the medical device 130. In an embodiment, the medical device 130 can include a first RFID tag 140A disposed on the stylet 132 and a second RFID tag 140B disposed on the packaging 138. In an embodiment, the stylet 132 can be configured to be disposed within a lumen of a needle, cannula, catheter, introducer, or the like. As shown, the stylet 132 is disposed within a lumen of an introducer 136 however this is not intended to be limiting. In an embodiment, a distal portion of the stylet 132 can be configured to extend into a vasculature of the patient. The fiber optic stylet 132 can be configured to map a tortuous pathway through the vasculature of the patient by determining a location or angle of flexion along an axis of the stylet 132. As will be appreciated, the fiber optic stylet 132 is exemplary and other modalities of mapping a vessel including impedance, conductance, or ultrasonic modalities are also contemplated.

In an embodiment, the stylet hub 134 can be configured to couple to a connector 114 that is communicatively coupled to the console 110. In an embodiment, the connector 114 provides fiber optic communication between the stylet 132 and the console 110. The console 110 can then be configured to receive and interpret optical signals from the stylet 132 to determine a map of the tortuous pathway through the vasculature. In an embodiment, the connector 114 can be coupled with different types of medical devices 130, e.g. different types of fiber optic stylet 132, medical devices 130, or the like.

In an embodiment, the connector 114 of the console 110 can include an RFID emitter 120 configured to provide an interrogation signal 122. The interrogation signal 122 can be a radio frequency electro-magnetic wave and can impinge on the RFID tag 140, associated with the medical device 130, e.g. within the stylet hub 134 or on the packaging 138. The interrogation signal 140 can induce or trigger a response signal 142 from the RFID tag 140 that can be received by the RFID emitter 120. In an embodiment, the RFID tag 140 can be a passive RFID tag that does not require any additional power source to provide a response signal 142. Instead, the interrogation signal 122 provides sufficient energy to actuate the RFID tag 140 and trigger a response signal 142. In an embodiment, the response signal 142 is a reflected interrogation signal 122 indicating the presence or absence of the RFID tag 140 within a predetermined range from the RFID emitter 120. Exemplary ranges between the RFID emitter 120 and the RFID tag 140, which can induce a response signal can be: <1 cm, between 1 cm and 1 m, between 1 m and 50 m, or greater than 50 m. However, it will be appreciated that greater or lesser ranges or different combinations of ranges are also contemplated.

In an embodiment, the response signal 142 includes additional or different information from the interrogation signal 122. The information can be stored on the RFID tag 140 and encoded to the response signal 142. In an embodiment, the RFID emitter 120 can "read" information from the RFID tag 140 that is encoded within the response signal 142. Exemplary information stored on the RFID tag 140 can include information about the medical device 130 such as make, model, batch number, serial number, dimensions, specifications, calibration information, combinations thereof, or the like, as described in more detail herein.

In an embodiment, the RFID emitter 120 can "write" information to the RFID tag 140. The information can be transferred to the RFID tag 140, encoded within the interrogation signal 122, to be store thereon. Exemplary information to transfer to the RFID tag 140 can include patient information, date, time, system information, console information, combinations thereof, or the like, as described in more detail herein. In an embodiment, the information transferred to the RFID tag 140 can then be provided to the RFID emitter 120 at a later time, or to a different RFID emitter 120A.

In an embodiment, the medical device 130 can be configured to write information to the RFID tag 140. The RFID emitter 120 can then read this information from the RFID tag 140 and transfer the information to the console 110. For example, a medical device 130 can be configured to determine a number of times a needle is inserted to the patient. Optionally, the medical device 130, tracking system, or the like can record additional information, e.g. a needle insertion location or the like and either write this information to the RFID tag 140 or communicate the information directly to the console 110.

In an embodiment, the RFID emitter 120 can be triggered to provide an interrogation signal 122. The RFID emitter 120 can be triggered by the console 110 to provide an interrogation signal 122, for example when information about a medical device 130 is required. In an embodiment, the RFID emitter 120 can be triggered in response to an action, or at a given time or time interval. In an embodiment, the RFID emitter 120 can be triggered to provide an interrogation signal 122 when the medical device 130 is coupled with the connector 114. In an embodiment, the RFID emitter 120 can be triggered to provide an interrogation signal 122 when the medical device 130 is disposed proximate the connector 114, or are disposed within the same sterile field. In an embodiment, the RFID emitter 120 can provide a constant interrogation signal 122. In an embodiment, one of the interrogation signal 122 or the response signal 142 can cross a sterile barrier to enter or exit a sterile field. For example, the medical device 130 can remain within a sterile field while the console 110 and connector 114 can remain outside of the sterile field.

Advantageously, the RFID emitter 120 can interrogate the RFID tag 140 while the medical device 130 is still disposed within the packaging 138. The console 110 can then determine the correct medical device 130 before being removed from the packaging 138. Optionally, the packaging 138 can provide a sterile barrier and maintain the medical device 130 within a sterile environment. Advantageously, the RFID emitter 120 of the connector 114 can interrogate the RFID tag 140 of the medical device 130 to automatically verify information about the medical device or calibrate the console 110. This can allow the sterile field to remain intact while the console 110 verifies information about the medical device 130. As a result, if any changes to the equipment are required these can be carried out prior to breaching the sterile field.

In an embodiment, the RFID emitter 120 can provide an interrogation signal 122 to a specific medical device 130, or towards a specific location relative to the RFID emitter 120. In an embodiment, the RFID emitter 120 can broadcast an interrogation signal 122 to impinge on one or more medical devices, e.g. a first medical device 130 and a second medical device 130A, proximate the RFID emitter 120. In an embodiment, the RFID emitter 120 can provide an interrogation signal 122 before, during, or after a procedure.

Advantageously, the system 100 can provide an interrogation signal 122 to induce a response signal 142 from an RFID tag 120 disposed on a medical device 130, e.g. stylet 132, to determine specific information about the stylet 132 and can automatically calibrate the tracking system 100 for the specific medical device 100 being used, for example on connection of the stylet 132 with the connector 114.

In an embodiment, a range of the RFID emitter 120 can be configured to trigger a response signal 142 when the medical device 130 is adjacent, or coupled to, the connector 114. The RFID tag 140 can provide information, e.g. calibration or identification information, specific to the medical device 130 to the RFID emitter 120 and the console 110. As such, the system 100 can automatically calibrate the console 110 to the specific medical device 130 attached thereto. This can save time and reduce the workload of clinicians by obviating manually entering such information to the console 110 either before, during or after a procedure. Further, errors in data entry, procedures, or in selecting incorrect calibration settings, or the like, are mitigated.

Figure 1B:
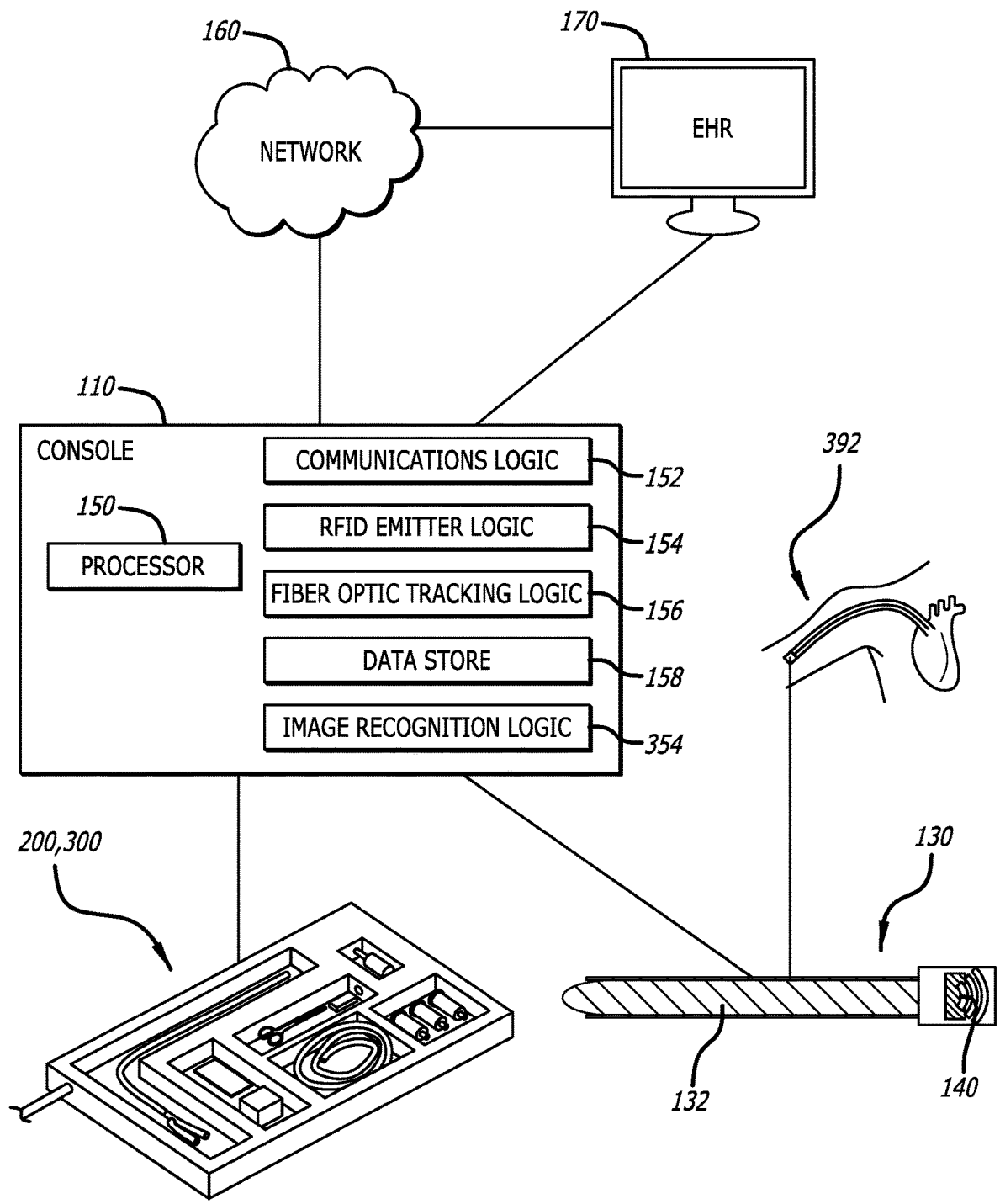
FIG. 1B shows the medical system of FIG. 1A communicatively coupled with a remote computing device, in accordance with embodiments disclosed herein.

FIG. 1B shows a schematic view of the RFID enabled system 100 communicatively coupled to one or more networked devices. In an embodiment, the console 110 can include one or more processors 150 and one or more logic modules. In an embodiment, the console 110 can include a communications logic 152 configured to communicatively couple the console 110 with the medical device 130, a network 160, or a remote computing device 170, e.g. an electronic health records (EHR) system, combinations thereof, or the like. The console 110 can be communicatively coupled either directly or indirectly with a network 160 or remote computing devices 170. As used herein, the network 160 can be a centralized or decentralized network, intranet, local area network (LAN), internet, a "cloud" based network, or the like. As used herein the remote computing device 170 can be one or more computing devices, servers, mainframe, hospital network, electronic health record system, or the like. Advantageously, the network 160 or remote computing device 170 can provide information to the console 110 e.g. patient health records, or the like. The console 110 can then use this information together with information from the medical device 130 to display up to date information to the user or advise the user on a correct protocol. For example, previous access sites 392 can be provided from the patient records and the console 110 can display a location for a new access site, which can then be confirmed by information from the medical device 130.

In an embodiment, the console 110 can include an RFID emitter logic 154 configured to send an interrogation signal 122 by way of the RFID emitter 120 and configured to receive and interpret a response signal 142 from the RFID tag 140. In an embodiment, the console 110 can include a fiber optic tracking logic 156 configured to send and receive information to or from the fiber optic stylet 132. As will be appreciated, the console 110 can include additional logic configured to be operatively coupled to additional structures, e.g. ultrasound logic configured to be operatively coupled to an ultrasound probe, a tip tracking logic configured to be operatively coupled to a tip tracking system, or the like. In an embodiment, the console 110 can include a data store 158 or similar non-transitory storage media configured to store information from the medical device 130, console 110, network 160, or remote computing device 170, combinations thereof, or the like.

In an embodiment, the RFID enabled system 100 can include one or more RFID tags 140 disposed on one or more medical devices 130 of different types. One or more RFID emitters 120 can be communicatively coupled with a console 110, and configured to interrogate the one or more RFID tags 140 to determine information about the medical devices 130 that are present. Advantageously, since the passive RFID tag 140 does not require any power supply, active communication logic, associated structures, or the like, the RFID tag 140 can be very small in size and relatively cheap to produce. As such, the RFID tag 140 can be included in a variety of disposable or single-use medical devices or equipment, as described in more detail herein.

As noted herein, the fiber optic stylet 132 is an exemplary medical device 130 and not intended to be limiting. In an embodiment, the one or more medical devices 130 that each include an RFID tag 140 can also include: Indwelling devices such as catheters, peripherally inserted central catheters (PICC), central venous catheters (CVC), midline catheters, intravenous (IV) catheters, or the like. Procedural devices such as ultrasound probes, trackable medical devices, vascular access management systems, intravenous (IV) infusion systems, infusion pumps, inventory management systems, stylets, needles, needle guides, introducers, guidewires, surgical instruments, hemostats, scalpels, medical lines, tubing, surgical towels, disinfection tools, dressing change kits, swabs, IV fluid bags, or the like. Packaging of the medical devices, such as kit type, device type, or the like. Maintenance devices such as catheter caps, dressings, CHLORAPREP™ swabs, SITE-SCRUB® IPA devices, or the like. Personnel identification equipment such as ID badges including personal details of the clinician, support staff, etc., patient bracelets including personal details of the patient, ID badges of visitors including personal details of the patients family, or the like. However, these examples are not intended to be limiting.

Information that can be stored on the RFID tag 140 and can be communicated to the RFID emitter 120 can include: Medical device identification such as make, model, serial number, batch number, kit number, or the like, of the medical device 130 or of a kit including one or more medical devices 130. Medical device specification information such as size, type, dimensions, catheter configuration such as lumen (number, dimensions, etc.) or French size, calibration information, fiber optic calibration file, tracking profile, or the like. Personnel information such as information or signature info about the clinician, patient, support staff, or visitors, or the like. Analytics or compliance information such as the order of equipment to be used for a procedure, time stamp for when a procedure is started or when a medical device is used, duration of the procedure, time since start of various events (e.g. CHLORAPREP™ application time), time since completion of various events (e.g. CHLORAPREP™ dry time), time from last procedure, devices used during procedure, devices recovered after procedure, initiation of scanning, initiation of catheter placement, time access was obtained, time catheter introduced, duration of navigation stage, tip confirmed, site dressing applied, or the like. As will be appreciated, a time stamp can be recorded by the console 110 when a response signal 142 is first detected for given medical device 130 indicating a presence of the medical device proximate the RFID emitter 120, or when a response signal 142 is no longer detected indicating an absence of the medical device proximate the RFID emitter 120. Post-procedure and identification information such as detecting the presence and accounting for surgical tools prior to closure of a surgical site, detecting the presence and accounting for surgical towels prior to closure of a surgical site, catheter trim length, or the like. Automatic device update information such as start time, duration time, or an indication of replacement time for dressing replacements, catheter placement, site cleaning, site scrubbing, medical line (e.g. IV or catheter) flushing, infusion information, or the like. However, this is not intended to be limiting.

In an embodiment, information can be written to the RFID tag 140 and can be communicated to the RFID emitter 120 at a later date, or to a different RFID emitter 120A. In an embodiment, information that can be written to the RFID tag 140 can include medical device identification, medical device specification information, personnel information, analytics or compliance information, post-procedure and identification information, or automatic device update information, as described herein.

In an embodiment, analytics or compliance information can further include the start date/time, finish date/time, duration, etc. of a procedure or action, for example, when a catheter or dressing was placed, site cleaning, site scrubbing, flushing time, flushing duration, flushing count, the order of operations of a procedure based on one or more RFID tags 140. Post procedural information can further include catheter trim length, catheter exit site marking, or the like. Identification information can further include information about the console(s) 110 being used with the medical device 130, such as device information or settings of the console 110.

In an embodiment, the console 110 can be communicatively coupled with additional consoles, computing devices, ultrasound systems, tip tracking systems, multi-modal tracking systems, infusion pumps, workstation, mobile device, handheld device, or the like being used with the medical device 130, information about these additional devices can also be written to the RFID tag 140. Identification information about these additional devices, computing platforms or software used by the additional devices can also be written to the RFID tag 140.

Exemplary multi-modal tracking systems can use magnetic, electromagnetic, ultrasonic modalities, combinations thereof, or the like. Details of exemplary multi-modal tracking systems can be found in U.S. Pat. Nos. 8,388,541, 8,781,555, 8,849,382, 9,445,743, 9,456,766, 9,492,097, 9,521,961, 9,554,716, 9,636,031, 9,649,048, 10,159,531, 10,172,538, 10,413,211, 10,449,330, 10,524,691, 10,751,509, 11,000,205, and U.S. Publication No. 2018/0116551, each of which are incorporated by reference in their entirety into this application.

In an embodiment, the information written to the RFID tag 140 or encoded in a response signal 142 can be stored and analyzed by the console 110. In an embodiment, the information described herein can be communicated by the console 110 either directly or indirectly with a remote location or remote computing device, for example a network 160, or electronic medical records (EMR) 170, intranet, internet, local area network (LAN), cloud-based network or the like. In an embodiment, the information described herein can be analyzed to assess compliance with regulation or operating procedures during a procedure, such as minimum cleaning times, dwell times not extended, etc. Further, the information can be used to track inventory of all devices present, devices used, devices disposed of, or devices retrieved during a procedure. This can ensure medical devices, surgical tools, surgical towels, disinfection tools, or the like, can be tracked and are not lost or miscounted. The information can be used for reporting of analytics of devices used, catheter trim length, amounts or counts of devices, fluids, or products used. This information can also be used for system optimization such as fiber optics calibrations, magnetic tracking profiles, success of outcomes, or the like, to improve future devices or systems, as described in more detail herein.

In an embodiment, the medical device 130 or console 110 can be communicatively coupled with additional medical device systems configured to detect and record additional information about a procedure. In an embodiment, this additional information can be written to the RFID tag 140 and can be read by the RFID emitter 120 to communicate the information to the console 110.

In an embodiment, the additional information may include a length of time the medical device is in use, a number of times a needle enters the body, tissue identification, "backwalling," venous/arterial determination to determine correct or incorrect access thereto. The additional information can include needle stick location or depth mapping (e.g. by name, image, video recording, 3D mapping, navigation path, etc.), access site location or depth mapping, azygos placement/deviation, catheter occlusion identification using artificial intelligence (AI), machine learning, neural networks, image recognition or the like.

In an embodiment, one of the medical device 130 or the console 110 may be configured to request additional information from a user. The user can provide this additional information by way of a user interface disposed on one of the medical device 130 or the console 110. As used herein a user interface can also include voice recognition or voice activation. In an embodiment, one of the medical device 130 or the console 110 can provide feedback to the user in the form of visual, audible, or tactile alerts. In an embodiment, the console 110 can be configured to record data from the medical device 130, medical kit 200, 300, or from remote computing devices 170 in real time, can maintain a rolling archive, and/or can save the information about the procedure for future analysis, as described herein.

Figure 2:
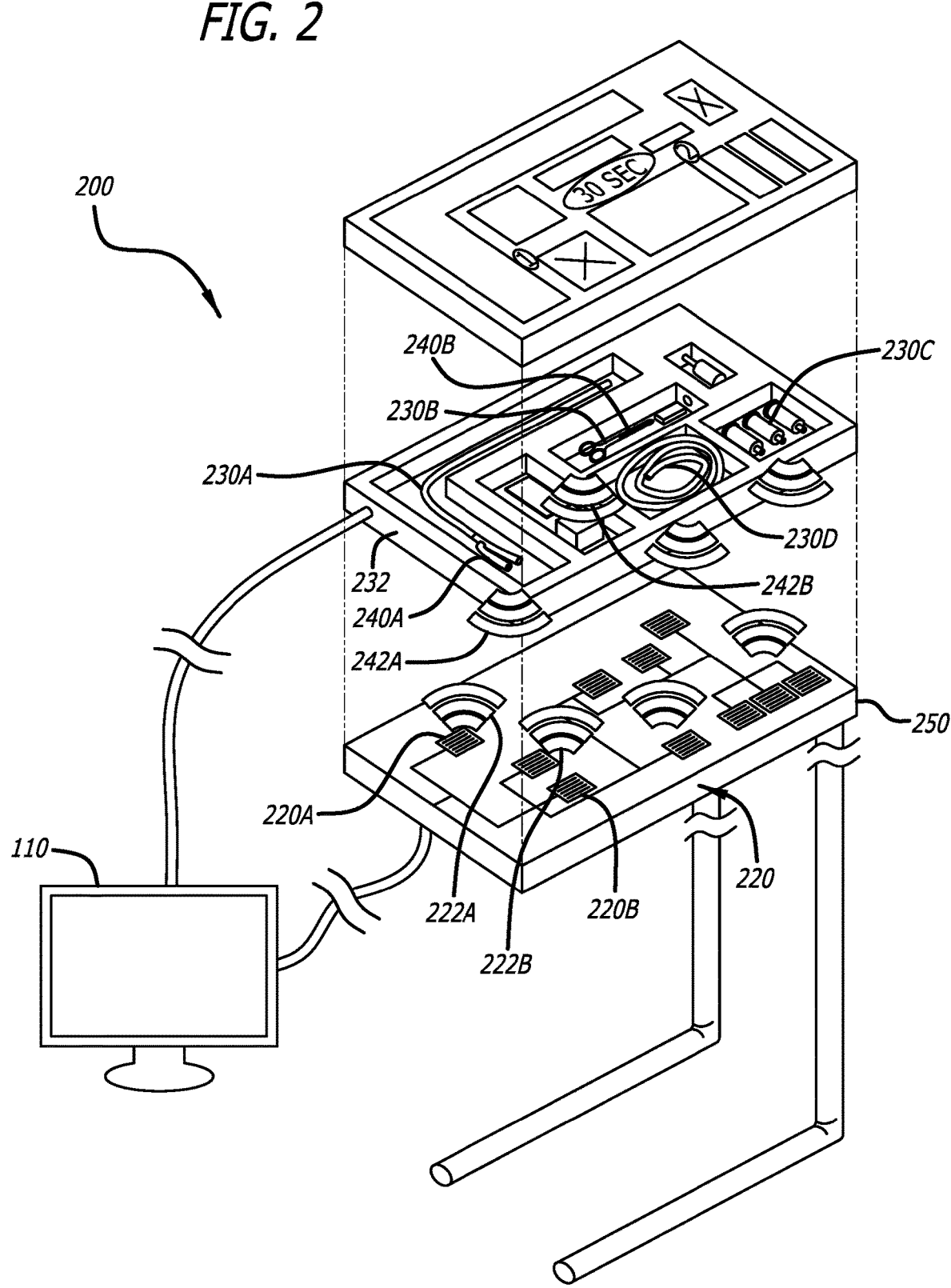
FIG. 2 shows an exemplary RFID enabled medical device kit, in accordance with embodiments disclosed herein.

FIG. 2 shows an exemplary RFID tracking system ("system") 200 including one or more medical devices 230 provided as a kit 232. As shown the medical devices 230 can include a catheter 230A, hemostat 230B, syringes 230C, tubing 230D, combinations thereof or the like. As described herein each of the medical devices 230 can include an RFID tag 240. For example, the catheter 230A can include a catheter RFID tag 240A, the hemostat 230B can include a hemostat RFID tag 240B, etc. However, it will be appreciated that these medical devices and associated RFID tags are exemplary and other medical devices may also be used, as described herein. The medical devices 230 can be provided as a kit 232 such as a tray including one or more compartments each configured to receive one of the one or more medical devices 230. In an embodiment, the kit 232 can include a flexible body or include one or more pockets, each pocket being configured to receive one of the one or more medical devices 230.

In an embodiment, the system 200 can include one or more RFID emitters 220 communicatively coupled with a console 110 and each configured to provide an interrogation signal 222 that can impinge on the RFID tag(s) 240. In an embodiment, the system 200 can further include a table 250, cart, roll stand, or the like. In an embodiment, the table 250 can include an RFID emitter 220 disposed therein. The table 250 can include a surface configured to receive the kit 232. More specifically, the table 250 can include an upper surface having one or more recesses or protrusions configured to align a lower surface of the kit 232 with the table 250. As such, a compartment of the kit, including a medical device 230 disposed therein, can be aligned with an RFID emitter 220 disposed in the table 250.

In an embodiment, the one or more RFID emitters 220 can be disposed in a flexible or rigid membrane that can be disposed below the tray kit 232, between the kit 232 and the table 250 or similar supporting surface. In like manner, the membrane can be aligned with tray kit 232 to align a compartment including a medical device 230 with an RFID emitter 220. In an embodiment, the one or more RFID emitters 220 can be disposed within the tray 232 itself and aligned with one or more compartments that includes a medical device 230. In an embodiment, one of the kit 232, the table 250, or membrane that include an RFID emitter 220 that is communicatively coupled with the console 110, and/or provide power to the kit 232, table 250, or membrane.

In an embodiment, the table 250 includes an RFID emitter 220 that provides an RFID interrogation signal 222 that can impinge on one or more of the RFID tags 240, e.g. catheter RFID tag 240A, hemostat RFID tag 240B, and can trigger one or more response signals 242, e.g. a catheter response signal 242A, a hemostat response signal 242B. In an embodiment, a first RFID emitter 220A can provide a first RFID interrogation 222A that can impinge on a first RFID tag 240, e.g. a catheter RFID tag 240A, to induce a first (e.g. catheter) response signal 242A. A second RFID emitter 220B can provide a second RFID interrogation 222A that can impinge on a second RFID tag 240, e.g. a hemostat RFID tag 240B, to induce a second (e.g. hemostat) response signal 242B.

In an embodiment, the RFID emitter 220 can provide a constant interrogation signal 222 that can trigger a response signal 242 when a medical device 230 including an RFID tag 240 is disposed proximate the RFID emitter 220, e.g. when the tray kit 232 is placed on the surface of the table 250 and aligned with the RFID emitter 220, or when the medical device 230 is returned to the compartment. In like manner, the system 200 can determine when a medical device 230 is being used by determining an absence of a response signal 242 when the medical device 230 is removed from the compartment.

In an embodiment, the system 200 can determine when the tray kit 232 is placed on the surface of the table, (e.g. pressure sensor, solenoid switch, light dependent capacitor, or the like) and can trigger the RFID emitter 220 to provide an interrogation signal 222 to impinge on the RFID tags 240. In an embodiment, the kit 232 itself can include an RFID tag 240 and can included identification information about the kit 232 including information about the medical devices disposed therein, as described herein.

In an embodiment, the system 200 can determine information about the procedure based on which medical device(s) 230 or kits 232 that are detected by the RFID emitter(s) 220. Further, the system 200 can determine information about the procedure based on the removal and replacement of the medical devices 230 from the kit 232. For example, a catheter medical device 230A can be removed from the tray kit 232 and no longer provides a response signal 243 indicating to the console 110 that the catheter is being used and a time stamp can be applied to this event. When the catheter 230A has been finished with and replaced to the tray kit 232, the system 200 can detect the presence of the catheter 230A based on the resumption of the response signal 242A. In an embodiment, the order with which each medical device 230 is used can be logged and analyzed by the system 200 to ensure compliance with regulations, standard operating procedures, or Information For Use ("IFU") protocols.

In an embodiment, the system 200 can use different modalities between the emitter 220 and the medical device 230. Exemplary modalities can include electrical, magnetic, or optical.

In an embodiment, the emitters 220 can be electrical sensors configured to align with an electrical contact disposed on the medical device 230. When the medical device 230 is disposed within the correct compartment, the compartment can be designed to align the medical device 230 with the electrical contact to complete an electrical circuit and determine the presence of the medical device 230 within the compartment or to transfer information between the medical device 230 and the tray 232 that is communicatively coupled with the console 110. In an embodiment, each of the medical devices 230 can include a passive, permanent magnet, and the tray 232 or table 250 can be configured to detect the presence of the magnet when the medical device 230 when disposed within the compartment.

Figure 3:
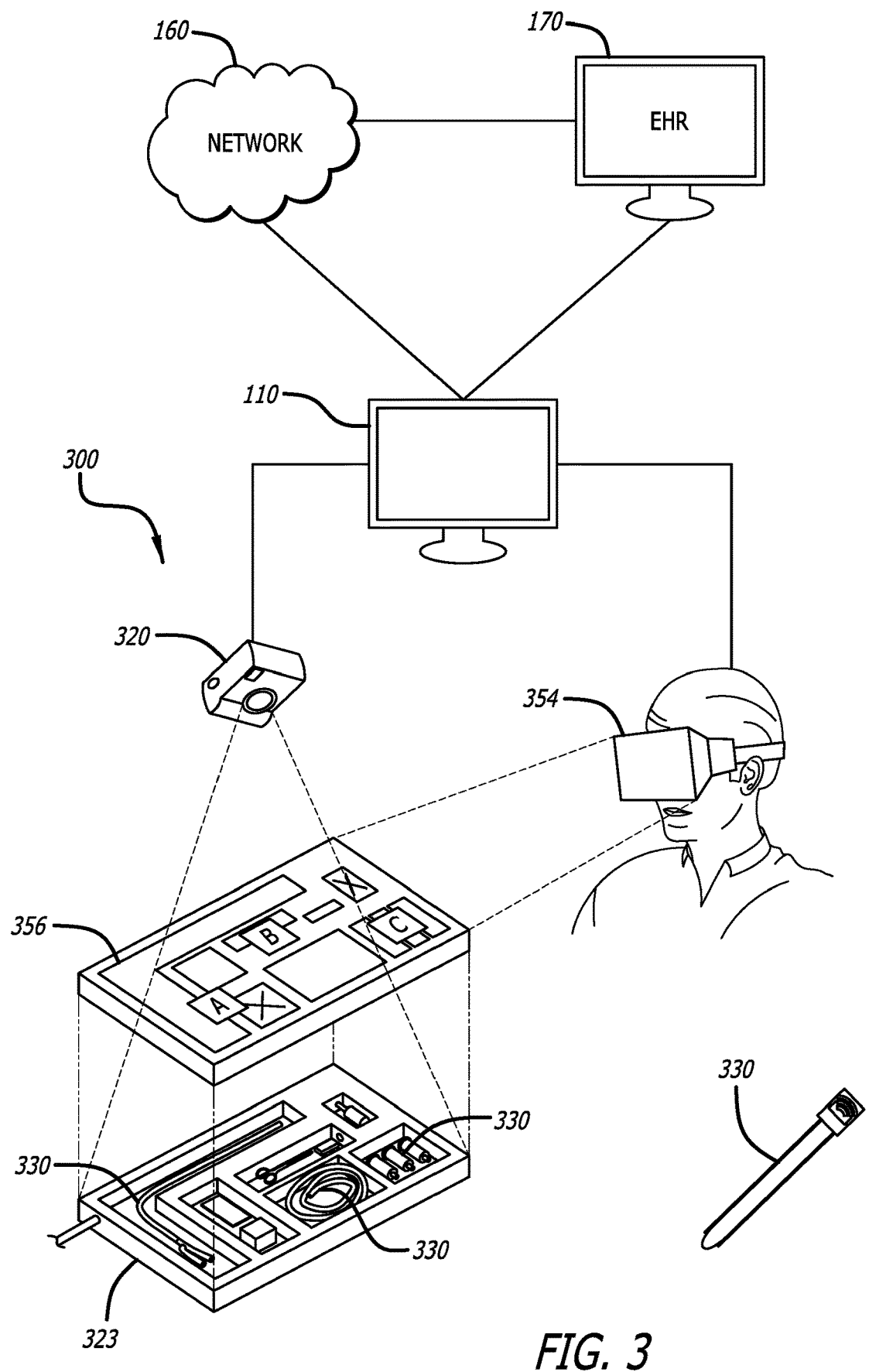
FIG. 3 shows an exemplary optically enabled medical device system, in accordance with embodiments disclosed herein.

FIG. 3 shows an embodiment of an optically enabled medical device system 300 including a medical device tray kit 332 including one or more medical devices 330 disposed therein. In an embodiment, an optical camera 340 can image the kit 332, e.g. from above. The camera 320 can be communicatively coupled with a console 110, as described herein. The console 110 can include an image recognition logic 354 configured to determine the presence or absence of a medical device 330 from the kit 332 based on image recognition of the kit 232. In an embodiment, the console 110 can use predetermined rule sets, artificial intelligence (AI), machine learning, neural networks, combinations thereof, or the like, to determine the presence or absence of the kit 332, or a medical device 330 disposed therein. For example, the console 110 can compare a first image of the kit 332 with a second image of the kit 332 and determine if a medical device 330 has been removed, and is therefore being used, or if a medical device 330 has been replaced to the kit. Time stamps can be applied to these events and information about the procedure, order of use, start time, end time, duration of use, duration of each step, order of use, rate of use, combinations thereof, or the like, can be determined as described herein.

In an embodiment, a surface of the compartment can include a symbol, for example, an alpha-numerical symbol, barcode, QR-code, or the like, which can be optically detected by the camera 320. When the medical device 330 is disposed within the compartment of the tray kit 332, the symbol can be obscured, when the medical device 330 is removed from the tray kit 332, indicating that it is being used, the symbol can be revealed and detected by the camera 320. In an embodiment, the symbol can include information encoded therein and interpreted by the camera 320 and console 110. As such, the system 300 can determine a start time, end time, duration, etc. for the medical device 330, as described herein.

In an embodiment, the system 300 can include a camera 320 configured for detecting a bar code or QR code disposed on ID badges of a clinician, support staff, patient wrist bands, or visitor badges and can retrieve information about personnel. In an embodiment, the system 300 including the camera 320 can be configured for facial recognition of clinicians, support staff, patients, and visitors.

In an embodiment, the system 300 can further include an augmented reality ("AR") viewer 354, such as AR goggles, AR heads up display ("HUD"), virtual reality ("VR") goggles, or the like. The AR viewer 354 can be communicatively coupled the console 110 and can provide a visual overlay 356 to the user indicating which medical device 330 to use, when to use, which order to use, how long to use, or where the medical device 330 should be returned to the kit 332. The system 300 can determine the information to provide to the AR viewer 354 by detecting the location or usage of the medical device 330 by RFID modality, magnetic, or optical modalities, as described herein. Advantageously, the AR viewer 254 can prompt a clinician as to the procedural steps to follow, which medical device to use, and can ensure that regulations, standard operating procedures, or IFU protocols, are abided by. Further, information about the procedure, how the medical device is used, etc. can be stored an analyzed to help improve future systems.

In an embodiment, the medical device kits 232, 332, and associated medical devices 230, 330 can configured for different procedures. Exemplary procedures can include: ultrasound imaging, ultrasound guided vascular access, needle tracking, probe tracking, fiber optic vessel mapping, needle path tracking, catheter tip location, catheter tip confirmation, multimodal tip location/confirmation, catheter placement, or the like.

For example, embodiments described herein can be used with a cleaning procedure for an ultrasound system capable of identifying anatomical targets and tracking medical instruments. An exemplary ultrasound kit 232 can be provided including one or more medical devices 230, e.g. one or more ultrasound probes. The system 200 can be configured to record and recognize the procedural steps during a cleaning process of the ultrasound kit after use. Optionally, the ultrasound system can remain connected while cleaning or the probe can be wireless coupled to the ultrasound system console, e.g. console 110 while the cleaning procedure takes place. Exemplary sterilization systems can include high level disinfection systems, the TROPHON® system, or the like. Embodiments disclosed herein can determine a cleaning start time, e.g. when an ultrasound probe is removed from the tray kit, an end time, e.g. when an ultrasound probe is returned to the tray kit, a duration of the cleaning process, the steps involved, the order of the steps, or combinations thereof, to ensure correct protocols for the cleaning process are adhered to.

Embodiments of the system 200, 300 can be capable of identifying procedural scenarios. For example, the system 200, 300 can identify when procedures taking longer than expected and can identify problems. The system can monitor a procedure duration, a number of times a device is used, number of needle sticks, or the like, that can indicate when a procedure is encountering a problem. The system can request additional information from the user to supplement this information and can highlight these procedures for further review, targeting the source of the problem and allow from future improvements to the system.

Figure 4:
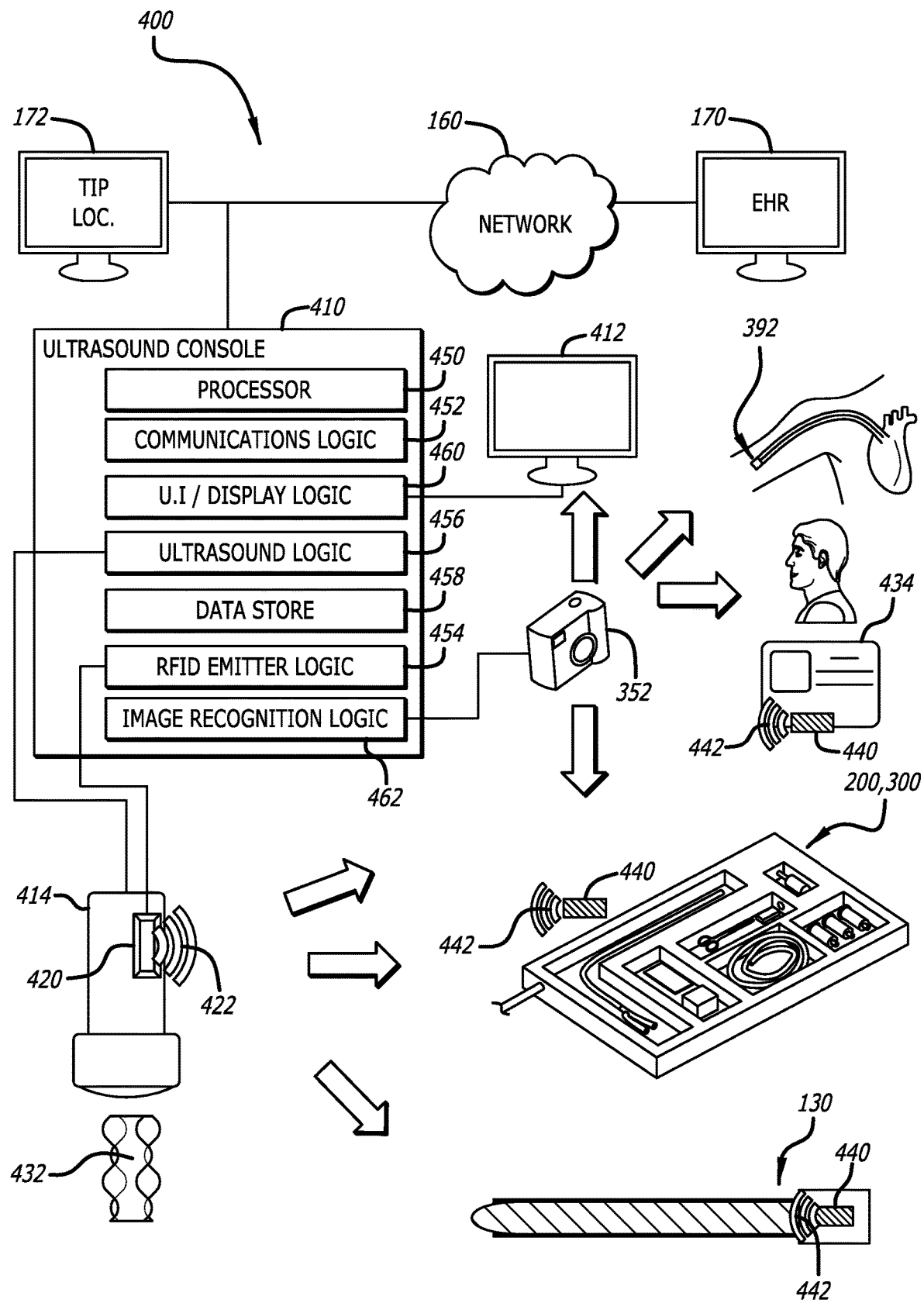
FIG. 4 shows an exemplary RFID or optically enabled ultrasound system, in accordance with embodiments disclosed herein.

FIG. 4 shows an embodiment of an RFID enabled ultrasound system ("ultrasound system") 400. The ultrasound system 400 generally includes an ultrasound console 410 including one or more processors 450 and one or more logic modules ("logic"). In an embodiment, the ultrasound console 410 can include a communications logic 452, an RFID emitter logic 454, an ultrasound logic 456, a data store 458, a user interface (U.I.) or display logic 460, and an image recognition logic 462. It will be appreciated that the ultrasound console 410 can include additional logic modules. In an embodiment, one or more of the communications logic 452, the RFID emitter logic 454, the ultrasound logic 456, the user interface (U.I.) or display logic 460, or the image recognition logic 462 can use artificial intelligence (A.I.), machine learning, neural networks, predetermined rule sets, combinations thereof, or the like.

The ultrasound console 410 can be communicatively coupled to an ultrasound probe 414 configured to emit and receive acoustic signals 432. The acoustic signals 432 can be communicated with an ultrasound logic 456 configured to generate an ultrasound image of a portion of a patient. The ultrasound image can be static or dynamic and can be stored to the data store 454 or can be displayed on a user interface device 412 (e.g. display) or the like, coupled to the ultrasound console 412. In an embodiment, the ultrasound console 410 can include an image recognition logic 462 coupled to the ultrasound logic 456 and/or the U.I./Display logic 460 configured to determine information directly from the ultrasound image.

The ultrasound system 400 can further include one or more RFID emitter(s) 420 communicatively coupled with an RFID emitter logic 454. In an embodiment, the RFID emitter 420 can be disposed on the ultrasound probe 414. In an embodiment, the RFID emitter 420 can be a stand-alone device communicatively coupled with one of the ultrasound console 410 or the ultrasound probe 414.

In an embodiment, the ultrasound console 410 can include a U.I./display logic 452 that is communicatively coupled with one or more user interface devices 412. Exemplary user interface devices can include a display, touch screen, microphone, voice recognition, keyboard, mouse, joystick, or similar devices configured to provide or receive information to/from a user. In an embodiment, the ultrasound console 410 can further include a communications logic 452 configured to communicatively couple the console 410 with one of a network 160, a remote computing device 170, additional medical device systems 172, combinations thereof, or the like. In an embodiment, the ultrasound console 410 can be communicatively coupled either directly or indirectly with a network 160, remote computing devices 170, or additional medical systems 172.

In an embodiment, the remote computing device 170 can be one or more computing devices, servers, mainframe, intranet, internet, hospital network, electronic health record system, combinations thereof, or the like. In an embodiment, the network 160 can be a centralized or decentralized network, intranet, local area network (LAN), internet, a "cloud" based network, or the like. In an embodiment, the one or more additional medical systems 172 can be a medical device system that can be used in conjunction with the ultrasound system 400 and can share information. Exemplary medical device systems can include tip location, tip confirmation, vessel mapping, fiber optic stylet mapping systems, needle tracking, probe tracking, needle path mapping, combinations thereof, or the like.

In an embodiment, the RFID emitter 420 can emit an interrogation signal 422. The interrogation signal 422 can impinge on one or more RFID tags 440 to provide a response signal 442. The response signal 442 can be received by the RFID emitter 422 can communicated to the RFID emitter logic 454. The RFID tag(s) 440 can be disposed on medical device(s) 130, medical device kit(s) 232, or the like. The RFID emitter 420 can detect the presence of the RFID tag 440 that are within range of the RFID emitter 420 by the presence or absence of the response signal 442. Further the RFID emitter 420 can read information stored on the RFID tag 440 or write information to the RFID tag 440, as described herein.

Embodiments of the RFID enabled ultrasound system 400 can be used with a variety of medical procedures, each requiring various medical devices 130 to be used with ultrasound system 400. Advantageously, the ultrasound system 400 can automatically detect and track which medical devices 130 are present, or being used by the clinician, based on the presence or absence of the response signal 442 detected by the one or more RFID emitters 420 communicatively coupled with the RFID emitter logic 454. These medical devices 130 can be reusable medical devices or disposable medical devices (needles, stylets, surgical towels, surgical swabs, etc.) Advantageously, the ultrasound console 410 can record the number of disposable medical devices used in a procedure and account for the return of each medical device to ensure that each are accounted for and none are lost.

Further the ultrasound system 400 can determine information about the medical device 130. For example, the medical device 130 can be a needle being used to access a vessel that is being imaged by the ultrasound probe 414. The ultrasound system 400 can automatically detect the presence of needle 130 proximate the probe 414 by the presence of the response signal 442, and determine information about the needle 130, e.g. size, material composition, etc. that can be used by the console 410 to automatically modify the ultrasound settings for the specific needle being used. In an embodiment, the ultrasound system 400 can determine which procedure is being performed based on the response signal 442 received from a medical device kit 200. The ultrasound console 410 can automatically modify the ultrasound settings of the ultrasound logic 456 to suit the procedure being carried out.

In an embodiment, the ultrasound system 400 can be used with a cleaning/sterilizing systems and procedures. Exemplary sterilization systems can include high level disinfection systems, the TROPHON® system, or the like. The RFID emitter 420 can determined the presence of a cleaning system based on the response signal 442 received from the RFID tag 440 associated therewith. The ultrasound system 400 can determine when the probe 414 is being cleaned based on the proximity of the probe 414 to the cleaning unit. The ultrasound system 400 can record a start time, finish time, or duration of the cleaning.

Optionally, the ultrasound probe 414 can remain communicatively coupled, e.g. wired or wirelessly, with the ultrasound console 410 while the cleaning is carried out. Embodiments disclosed herein can determine a cleaning start time, e.g. when the ultrasound probe 414 is disposed in the cleaning system bay, an end time, e.g. when the ultrasound probe 414 is removed from the cleaning system, a duration of the cleaning process, the steps involved, the order of the steps, or combinations thereof, to ensure correct protocols for the cleaning process are adhered to.

In an embodiment, the ultrasound system 400 can determine which clinicians, support staff, or patients are present for a procedure. For example, an RFID tag 440 can be disposed in an I.D. badge 434, patient wrist band, or the like. The ultrasound system 400 can determine which clinicians, staff, or patients are present based on the number of response signals 442 or the information encoded within the response signal 442. The ultrasound system 400 can record this information as part of the procedural information. Further, the ultrasound system 400 can query additional databases located on a network 160 or remote computing device 170, e.g. EHR, to retrieve additional information about the clinician or patients present. For example, the RFID tag 440 can provide a patient ID number and/or a clinician ID number. The ultrasound console 410 can then query a hospital network to retrieve patient health records based on the patient ID number, to confirm identity, identify pre-existing conditions, or the like. The ultrasound console 410 can then provide information about the patient to the clinician before, during, or after the procedure.

In an embodiment, the ultrasound system 400 can be communicatively coupled with a camera 352. The camera 352 can provide images to an image recognition logic 462 disposed on the ultrasound console 410. The image recognition logic 462 can be configured to detect and interpret information from images provided by the camera 352, for example bar codes or "QR" codes disposed on ID badges 434, patient wrist bands, medical device kits 300, or medical devices, as described herein. In an embodiment, the image recognition logic 462 can be configured for facial recognition, fingerprint recognition, iris recognition, or the like to determine the identity of clinicians, support staff, patients, or the like who are present for a procedure. In an embodiment the image recognition logic 462 can then use information detected in the image to query additional databases, e.g. EHR 170, to retrieve additional information. In an embodiment, the image recognition logic 462 can determine the presence or absence of a medical device 330, or the type of procedure carried out, based on an image of a medical device kit 323. In an embodiment, the ultrasound console 410 can be communicatively coupled with an additional medical device system 172 such as an RFID enabled medical device kit 200 or an optically enabled medical device kit 300, as described herein.

In an embodiment, the ultrasound console 410 can be configured to determine procedural scenarios based on the medical device(s) 130 used, the procedure order carried out, or a deviation from a procedure, in the order of medical device usage, or time taken. For example, the ultrasound console 410 can determine a "difficult stick" vessel-access procedure based on the length of time the access needle medical device 130 was used, the number of times the needle 130 entered the body, e.g. by tissue recognition needle information, image recondition by the camera 354, or image recognition of the ultrasound display 412, or the like. Further the console display 412 can provide a prompt to a clinician to request additional information about the procedure, problems encountered, number of failed attempts, etc.

In an embodiment, the ultrasound console 410 can determine a "mis-positioned" procedure, an accidental vein/artery access, or "backwalling" based on deviation in location or depth of the needle stick from a target location. As used herein, "backwalling" includes over penetration of a target vessel to penetrate a far wall of the vessel. For example, the ultrasound console 410 can retrieve information about the medical devices 130 or kits 200 being used to determine or confirm the procedure being carried out or identify the target vessel. The ultrasound system 400 can then update the system settings accordingly. Further, the image recognition logic 462 can review information from the ultrasound logic 456 or the U.I./Display logic 460 to determine a location, orientation, or trajectory of the needle and a location of the target vessel and determine if the needle is aligned with, or has correctly accessed the target vessel, or not.

For example, the ultrasound console 410 can retrieve information from the medical device 130 or the medical device kit 200 that the procedure being carried out is a central venous catheter (CVC) placement. The ultrasound console 410 can automatically update the ultrasound system 400 settings for imaging and identifying the target vessel and/or vessel access medical devices. The image recognition logic 462 can review ultrasound information and determine if the needle is accessing the target vessel correctly, or is targeting an incorrect vessel such as an artery or an azygos vein. In an embodiment, the ultrasound console 410 can differentiate between arterial or venous target vessels using Doppler imaging. In an embodiment, the ultrasound console 410 can retrieve additional information from additional medical systems 172, e.g. a tip location system, needle tracking system, or tissue differentiation needles (e.g. "smart" needles), to further improve the accuracy of needle tracking or trajectory.

The ultrasound console 410 can then provide a visual, audible, or tactile alert to the clinician if the access placement is incorrect.

Similarly, the ultrasound console 410 can identify medical device(s) 130 or medical device kits 200 that are used for arterial access or venous access and can modify the procedure, target vessels, or ultrasound system settings 400 to suit. In an embodiment, the image recognition logic 462 can review ultrasound information to automatically identify catheter occlusions for medical devices 130 (e.g. catheters) being imaged.

In an embodiment, the ultrasound console 410 can record and store information about the medical device 130 or the procedure carried out to the data store 458 and/or communicate the information with network(s) 160 or remote computing devices 170. The ultrasound console 410 can then compare medical device equipment information or procedural information with predetermined equipment and procedure models to determine compliance with regulations, standard operating procedures, or IFU protocols. For example, the ultrasound console 410 can record excessive vessel attempts, duration of cleaning, the order of operations, the targeting of an incorrect vessels, vessel confirmation (smart needle), procedural step timing, or the like and can alert the clinician in real time if the equipment or procedural information is deviating from the predetermined standard operating procedures or the like. The ultrasound console 410 can alert the clinician using visual, audible, or tactile alerts. Compliance information can either be determined after the procedure has been completed, or can be notified in real-time as the procedure is carried out.

In an embodiment, the ultrasound system 400 can record and replay a subset of the procedural information, or can be configured to selectively record information about the procedure. In an embodiment, the ultrasound system 400 can be configured to include an on/off recording selection, rolling archive, or request input from the clinician as to whether to save information recorded about the procedure.

In an embodiment, the ultrasound console 410 can record a location of a needle access site for the patient. The access site information 392 can be recorded by the U.I. Display logic 460 from input from the clinician, image recognition information from the optical camera 352 and image recognition logic 462, image recognition from ultrasound image information, the probe 414, and the ultrasound logic 456, information from the medical device and the RFID emitter logic 456, or from additional medical device systems 172, e.g. tip location systems, or the like. The access site information can be stored as reference points, co-ordinates, 3D renderings, video or images, or the like.

Access site information 392 can be stored locally on the data store 458 and or communicated to electronic health records (EHR) on a remote computing device 170. The access site information 392 can then be automatically retrieved and presented to the clinician on the display 412 when the ultrasound system 400 determines that a medical device 130, kit 232 or associated procedure requires the access site information. Advantageously, the ultrasound system 400 can indicate to the clinician where previous access sites were and identify different access sites to prevent the buildup of scar tissue for a patient.

In an embodiment, the ultrasound console 410 can record and identify procedural steps including a start of the procedure e.g. initiation of ultrasound scanning, initiation of placement, exit site management of tunneled catheters, catheter trim length, time or location of access obtained, time or location of catheter introduced, duration of navigation, total vasculature map (e.g. fiber optic stylet information, impedance/conductance information, ultrasound information), information from additional medical systems 172 (e.g. tip confirmation), site dressing used (e.g. RFID enable site dressing medical device 130, as described herein), combinations thereof, or the like. The ultrasound console 410 can record the procedural information and optionally alert the clinician in real time if the equipment or procedural information is deviating from the predetermined standard operating procedures or the like. The ultrasound console 410 can alert the clinician using visual, audible, or tactile alerts.

In an embodiment, the ultrasound system 400 can determine a post-procedural model detailing information, events, timings, etc. of procedures to be carried out after the procedure is complete. The ultrasound system 400 can identify placement of a midline catheter procedure from the medical device(s) 130 or medical device kit(s) used, e.g. kit 232. The ultrasound system 400 can record placement procedure information as described herein, identify when the procedure is complete and record information to the patient's EHR located on the remote computing device 170, as described herein. Further, the ultrasound system 400 can identify a post-procedure model. The post procedure model can identify site dressing changes, flushing instances, flushing volumes, access timestamps, infusion info (volumes, fluids, etc.), catheter replacement, time of occlusions incurred, time of patency resolutions, combinations thereof, or the like.

For example, the ultrasound system 400 can identify, using RFID or optically enabled medical devices, which specific site dressing medical device 130 was used and when it was applied. The post-procedure model can identify when the site dressing 130 will need to be changed and if the change was carried out. Similarly, the post-procedure model can identify when the intravenous line was last flushed, which package of flushing solution was used and when the intravenous line will need to be flushed next.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An RFID enabled medical device kit, comprising:
   a tray including a compartment configured to contain a plurality of medical devices;
   an RFID tag associated with each medical device of the plurality of medical devices; and
   an RFID emitter communicatively coupled to a console and configured to provide an interrogation signal that can impinge on each RFID tag to trigger a response signal, the response signal configured to provide information to the console about each medical device, the information including an order with which each medical device of the plurality of medical devices is to be used for a procedure,
   wherein the RFID emitter is disposed within a support surface configured to support the tray, the support surface including a table, a cart, a rolling stand, or a flexible membrane.

2. The RFID enabled medical device kit according to claim 1, wherein the RFID emitter is disposed within the tray.

3. The RFID enabled medical device kit according to claim 1, wherein the RFID emitter is configured to provide a first interrogation signal which can induce a first response signal from a first medical device and a second response signal from a second medical device.

4. The RFID enabled medical device kit according to claim 1, wherein:
   the RFID emitter is a first RFID emitter configured to provide a first interrogation signal to a first medical device of the plurality of medical devices, wherein the first interrogation signal can induce a first response signal from the RFID tag associated with the first medical device, and
   the RFID enabled medical device kit further includes:
      a second RFID emitter configured to provide a second interrogation signal to a second medical device of the plurality of medical devices, wherein the second interrogation signal can induce a second response signal from the RFID tag associated with the second medical device.

5. The RFID enabled medical device kit according to claim 1, wherein the RFID emitter is configured to trigger the response signal when the RFID tag is within a range of less than 1 cm.

6. The RFID enabled medical device kit according to claim 1, wherein each medical device can include one of an indwelling device, a procedural device, a packaging of each medical device, a maintenance device, or a personnel identification equipment.

7. The RFID enabled medical device kit according to claim 1, wherein the information provided to the console includes one of medical device identification, medical device specification information, personnel information, analytics information, compliance information, post-procedure and identification information, or automatic device update information.

8. The RFID enabled medical device kit according to claim 1, wherein the RFID emitter is configured to write information to the RFID tag.

9. The RFID enabled medical device kit according to claim 8, wherein information written to the RFID tag includes one of medical device identification, medical device specification information, personnel information, analytics information, compliance information, post-procedure and identification information, or automatic device update information.

10. The RFID enabled medical device kit according to claim 1, further including an augmented reality viewer communicatively coupled to the console and configured to provide an image overlay of the RFID enabled medical device kit to indicate the order with which each medical device of the plurality of medical devices is used.

11. The RFID enabled medical device kit according to claim 1, wherein the console is configured to log the order, and analyze the order in conjunction with one or more of regulations, standard operating procedures, or an information for use protocol to ensure compliance therewith.

12. The RFID enabled medical device kit according to claim 1, wherein the information includes a post-procedure accounting that one or more of the plurality of medical devices are returned to the tray.

13. The RFID enabled medical device kit according to claim 1, wherein the information includes medical device procedure information based on removal of at least one of the plurality of medical devices from the RFID enabled medical device kit and replacement of the at least one of the plurality of medical devices to the RFID enabled medical device kit.

14. The RFID enabled medical device kit according to claim 13, wherein the information includes a use period of the at least one of the plurality of medical devices between the removal and the replacement.

15. The RFID enabled medical device kit according to claim 8, wherein the information written to the RFID tag includes the order.

* * * * *